United States Patent
Tamura

(10) Patent No.: US 8,435,182 B1
(45) Date of Patent: *May 7, 2013

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 570 days.

This patent is subject to a terminal disclaimer.

(21) Appl. No.: 12/494,019

(22) Filed: Jun. 29, 2009

Related U.S. Application Data

(60) Provisional application No. 61/102,058, filed on Oct. 2, 2008.

(51) Int. Cl.
*A61B 8/00* (2006.01)
(52) U.S. Cl.
USPC .................. 600/454; 600/437; 600/453
(58) Field of Classification Search .......... 600/437, 600/441, 453, 454, 455
See application file for complete search history.

(56) References Cited

U.S. PATENT DOCUMENTS

| | | | |
|---|---|---|---|
| 6,733,454 B1 * | 5/2004 | Bakircioglu et al. | 600/453 |
| 2006/0184032 A1 * | 8/2006 | Shiki | 600/454 |

OTHER PUBLICATIONS

Deane et al., "Doppler ultrasound: principles and practice", 2002, accessed online Feb. 2, 2012 at http://www.centrus.com.br/DiplomaFMF/SeriesFMF/doppler/capitulos-html/chapter_01.htm.*

* cited by examiner

*Primary Examiner* — James Kish
*Assistant Examiner* — Christopher Cook
(74) *Attorney, Agent, or Firm* — Buckley, Maschoff & Talwalkar LLC

(57) ABSTRACT

A system for ultrasound imaging may include acquisition of color Doppler data associated with a pulse repetition frequency ($f_{PRF}$) and a baseline shift, selection of a frame of the color Doppler data associated with low flow velocity, determination, based on the selected frame, of a first area of non-aliased flow velocities and a first direction of the non-aliased flow velocities, and detection, in another frame of the color Doppler data, of a first transition between one or more velocities of the first area and one or more velocities of an adjacent second area. A second transition may be detected between the second area and an adjacent third area of the color Doppler data, and a velocity corresponding to a Doppler shift frequency of $f_{PRF}$ is subtracted from or added to each of the flow velocities of the second area.

25 Claims, 14 Drawing Sheets

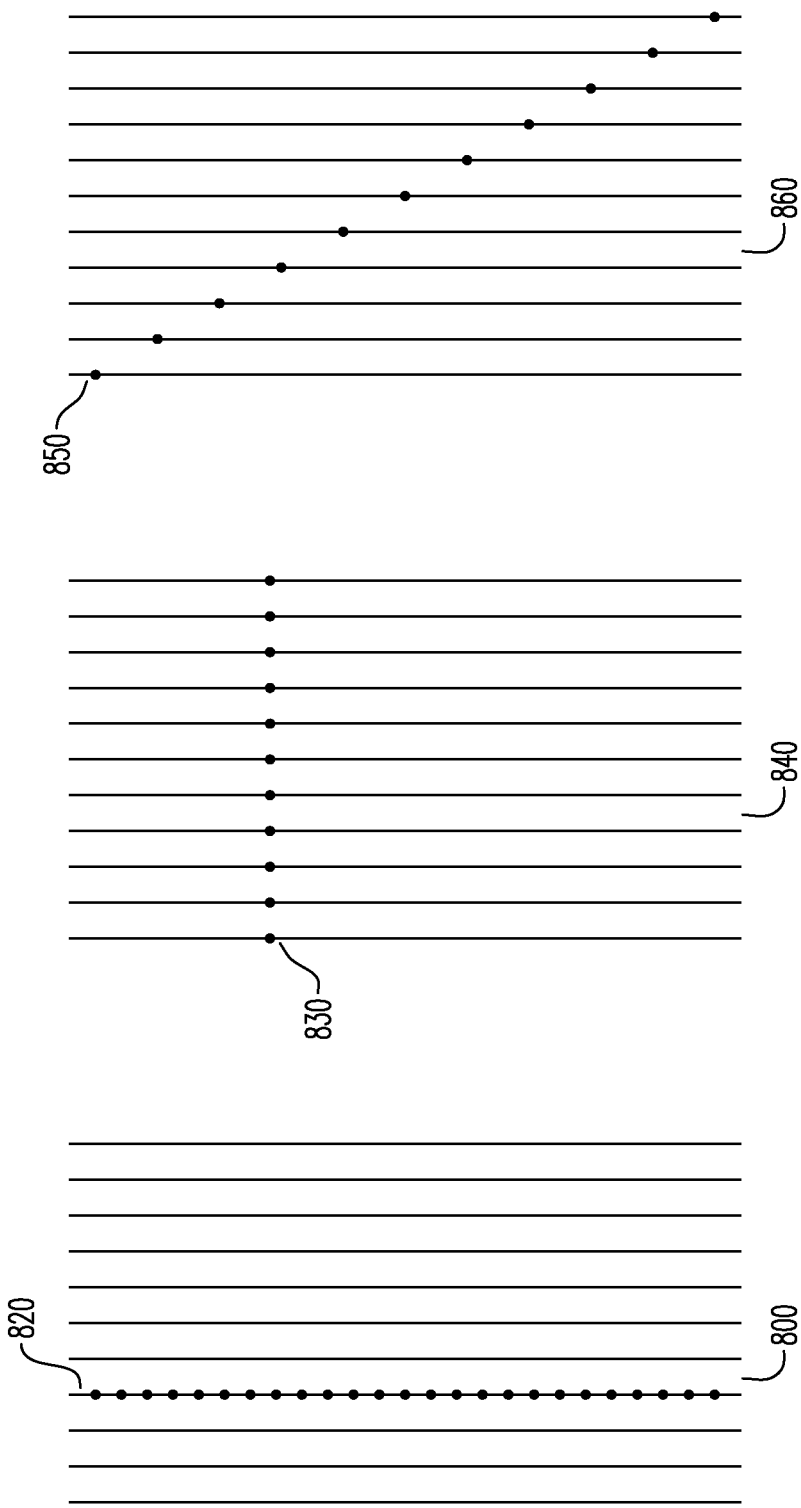

Figure 11A      Figure 11B      Figure 11C

METHODS AND APPARATUS FOR ULTRASOUND IMAGING

CROSS-REFERENCE TO RELATED APPLICATION

The present application claims priority to U.S. Provisional Patent Application Ser. No. 61/102,058, filed on Oct. 2, 2008 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for color flow imaging.

Ultrasound is used to image various internal structures, including but not limited to the heart, the liver, a fetus, and blood vessels. For diagnosis of cardiovascular diseases, color Doppler (or color flow) imaging is usually used to visualize blood flow in the heart or blood vessels. Abnormal conditions often increase blood flow velocity in comparison to that under normal conditions. The increased velocity may result in aliasing within a corresponding color Doppler image. Color Doppler uses a pulse ultrasound technology for its spatial sampling capability, which limits the maximum frequency which can be detected without experiencing aliasing. The pulse repetition frequency (PRF), which is also the sampling frequency, sets the maximum frequency limitation. This limitation, in turn, limits the maximum blood flow velocity which can be measured without exhibiting aliasing. This limitation may be particularly problematic in cardiac cases. For example, the PRF cannot be set high enough to measure abnormally high blood velocities that occur at substantial imaging depths such as, for example, regurgitation jets across heart valves. Therefore, under abnormal cardiac conditions, color Doppler often exhibits aliasing, thereby reducing the reliability of any diagnosis based on the blood flow image. Thus, there exists a need to address this aliasing problem.

SUMMARY

Some embodiments provide a system, method, apparatus, and means for ultrasound imaging including acquisition of color Doppler data associated with a pulse repetition frequency ($f_{PRF}$) and a baseline shift, selection of a frame of the color Doppler data associated with low flow velocity, determination, based on the selected frame, of a first area of non-aliased flow velocities and a first direction of the non-aliased flow velocities, and detection, in another frame of the color Doppler data, of a first transition between one or more velocities of the first area corresponding to Doppler shift frequencies greater than $$\frac{f_{PRF}}{2}$$

minus a first positive preset value minus the baseline shift if the first direction is positive or plus the baseline shift if the first direction is negative and one or more velocities of an adjacent second area of the color Doppler data in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive.

A second transition may be detected between the second area and an adjacent third area of the color Doppler data representing non-zero flow velocities in the first direction, and, if the second direction is positive, a velocity corresponding to a Doppler shift frequency of $f_{PRF}$ is subtracted from each of the flow velocities of the second area. If the second direction is negative, the velocity corresponding to a Doppler shift frequency of $f_{PRF}$ is added to each of the flow velocities of the second area.

According to other aspects, color Doppler data associated with a pulse repetition frequency ($f_{PRF}$) and a baseline shift is acquired, a frame of the color Doppler data associated with low flow velocity is selected, a first area of non-aliased flow velocities and a first direction of the non-aliased flow velocities are determined based on the selected frame, and one or more velocities of the first area and in the first direction in a second frame of the color Doppler data are detected, the one or more velocities corresponding to Doppler shift frequencies greater than $$\frac{f_{PRF}}{2}$$

minus a first positive preset value minus the baseline shift if the first direction is positive or plus the baseline shift if the first direction is negative.

A first transition between the one or more velocities of the first area in the second frame and one or more velocities of the first area in a third frame of the color Doppler data temporally-adjacent to the second frame is then detected, the one or more velocities of the first area in the temporally-adjacent third frame being in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive. Next, a second transition between the one or more velocities of the first area in a fourth frame and one or more velocities of the first area in a fifth frame of the color Doppler data temporally-adjacent to the fourth frame is detected, the one or more velocities of the first area in the temporally-adjacent fifth frame representing non-zero flow velocities in the first direction;

A velocity corresponding to a Doppler shift frequency of $f_{PRF}$ is subtracted from each of the flow velocities of the one or more velocities of the first area in the third frame, the fourth frame, and each frame temporally between the third and fourth frame if the second direction is positive, and a velocity corresponding to a Doppler shift frequency of $f_{PRF}$ is added to each of the flow velocities of the one or more velocities of the first area in the third frame, the fourth frame, and each frame temporally between the third and fourth frame if the second direction is negative.

BRIEF DESCRIPTION OF THE DRAWINGS

FIG. 8A: Aliasing detection in a vertical direction using color flow lines.

FIG. 8B: Aliasing detection in horizontal direction using color flow lines.

FIG. 8C: Aliasing detection in a diagonal direction using color flow lines.

FIG. 11A: Color-coded Doppler shift frequency (velocity) scale with no baseline shift.

FIG. 11B: Color-coded Doppler shift frequency (velocity) scale with a baseline shift of $$\frac{f_{PRF}}{4}.$$

FIG. 11C: Color-coded Doppler shift frequency (velocity) scale with a baseline shift of $$-\frac{f_{PRF}}{4}.$$

DETAILED DESCRIPTION

Figure 1A:
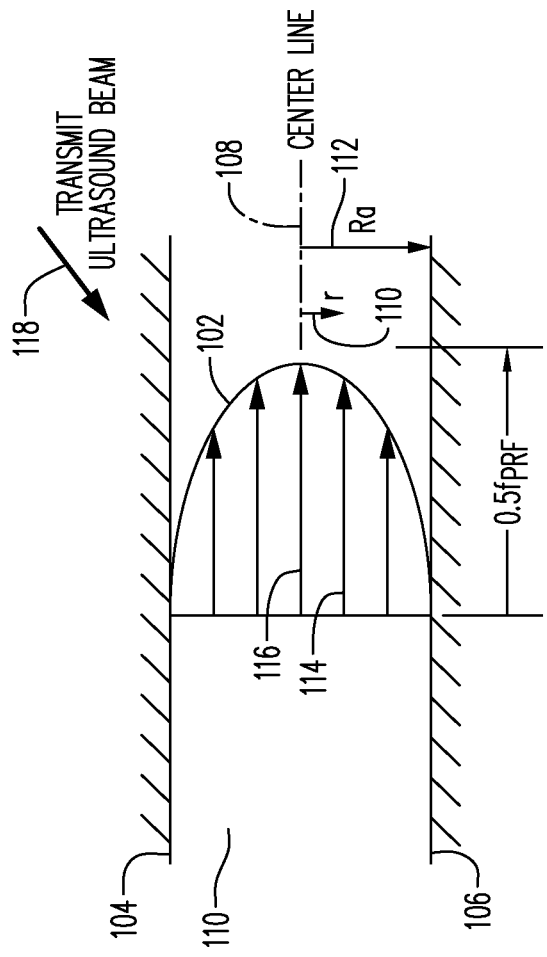
FIG. 1A: Blood velocity distribution in a vessel and transmit ultrasound beam direction.

Embodiments will be described with reference to the accompanying drawing figures wherein like numbers represent like elements throughout. Before embodiments of the invention are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that embodiments are not limited to any particular software language described or that is implied in the figures. One of ordinary skill in the art will understand that a variety of alternative software languages may be used for implementation of some embodiments. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

Ultrasound is transmitted by an ultrasound transducer into a human body to image various internal structures, including but not limited to blood vessels, a fetus, and the heart. Scatterers in tissue scatter the ultrasound and the scattered ultrasound is returned to the transducer. A receive beamformer creates ultrasound beams and a post-processor creates an image of tissues from the amplitude of the returned ultrasound signal as a B-mode image.

Blood vessels or the heart are often imaged, since they indicate cardiovascular conditions of patients. Blood flow information is usually acquired using color Doppler and spectral Doppler techniques.

Color Doppler is a two-dimensional imaging technique commonly used for imaging blood flow by sending ultrasonic waves into the blood flow and detecting the scattered ultrasound from the moving red cells. It consists of many beams similar to a B-mode image. A description of a color Doppler technique now follows; embodiments are not limited to the specific details therein.

In order to detect flow velocity, color Doppler transmits ultrasound signals several times per position to detect motion. To create a two-dimensional flow image, the transmit position is shifted by sub-millimeters, or about the order of an ultrasound wavelength. The transmit position shifting is repeated about 100 times to cover several centimeters and to create a two-dimensional flow image in linear and convex formats. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. Received beamformed RF ultrasound signals undergo quadrature demodulation resulting in complex, Doppler I-Q signals.

In a color Doppler technique, the ultrasound is transmitted at a pulse repetition frequency (PRF) and the blood flow velocity is detected as the shift in frequency (Doppler shift frequency) in the received ultrasound signal. The received ultrasound is mixed with in-phase (0 degrees) and quadrature (90 degrees) reference signals of the same frequency as the transmit ultrasound frequency. After low-pass filtering high frequency components (e.g., second harmonics), only the baseband signals are obtained. Wall filtering (i.e., high-pass filtering) is applied to the baseband signals to remove strong clutter noise from tissue and slowly moving tissues such as blood vessel walls, resulting in complex I-Q Doppler signals. The wall filtering is performed because the Doppler I-Q signals may contain blood flow signal components as well as stationary tissue signal components. The stationary components are typically 30-40 dB greater than the blood flow components. Therefore, it is desirable to reduce or eliminate the stationary signal components in order to detect blood flow accurately.

Generally, the wall-filtered complex I-Q signal is used to derive the Doppler shift frequency because the Doppler shift frequency and the blood velocity have the following relationship $$\Delta f = \frac{2 f_t v \cos\theta}{c}, \quad (1)$$

where $\Delta f$ is the Doppler shift frequency, $f_t$ is the transmitted frequency, $v$ is the blood velocity, $\theta$ is the angle between the ultrasound beam direction and the velocity vector and $c$ is the speed of sound.

In the case of color Doppler, the number of the sampled signals is limited to only about 10. Therefore, an auto-correlation technique is usually used to determine the phase differences between the wall-filtered I-Q signal and then to determine the Doppler shift frequency and the blood flow velocity as follows. The color Doppler's I-Q signals $z(n)=x(n)+jy(n)$ are used to calculate "auto-correlation" R as shown in the following equation, where $z(n)$ is the wall-filtered complex I-Q Doppler signal, $x(n)$ is the in-phase (real) signal, $y(n)$ is the quadrature phase (imaginary) signal, n indicates the signal number, j is the imaginary unit and * indicates the complex conjugate.

$$R = \Sigma z(n) \cdot z^*(n-1) \quad (2)$$

The real (Real(R)) and imaginary (Imag(R)) parts of R are used to obtain the phase $\phi$ as shown in the following equation.

$$\varphi = \tan^{-1} \frac{\text{Imag}(R)}{\text{Real}(R)} \quad (3)$$

Since $\tan^{-1}$ usually provides only $-0.5\pi$ to $0.5\pi$, the position of complex value R in the complex coordinate may be also used to derive $\phi$ in the range of $-\pi$ to $\pi$. The phase $\phi$ is then related to the Doppler shift frequency as shown in the following equation.

$$\Delta f = \frac{\varphi f_{PRF}}{2\pi} \quad (4)$$

Other techniques can be used to obtain the phase and the Doppler shift frequency and the blood flow velocity. The Doppler shift frequency indicates the blood flow velocity. Additionally, the power of the high-pass filtered Doppler I-Q signals indicates the existence of blood flow and the variance of the data indicates turbulence.

Because the color Doppler signals are obtained by the pulsed ultrasound (and also sampling) technique, sampling theory dictates a maximum frequency limit. The maximum frequency is generally half of the pulse repetition frequency (PRF) or $f_{PRF}$. Since the autocorrelation is performed on the complex I-Q Doppler signals, blood flow velocity in a negative direction appears in the negative frequency domain. Therefore, the color Doppler frequency includes negative frequencies that correspond to negative velocities. For example, the Doppler shift frequency usually has a range of $$-\frac{f_{PRF}}{2}$$

to $$\frac{f_{PRF}}{2},$$

which in turn corresponds to a range of negative and positive maximum velocities.

Some embodiments employ other Doppler shift frequency ranges. For example, the range may incorporate a "baseline shift" in which the center frequency of the range is not equal to zero. In some embodiments, the baseline shift may be selected from a range of frequencies between $$-\frac{f_{PRF}}{2}$$

and $$\frac{f_{PRF}}{2}.$$

Figures 11A, 11B, 11C:
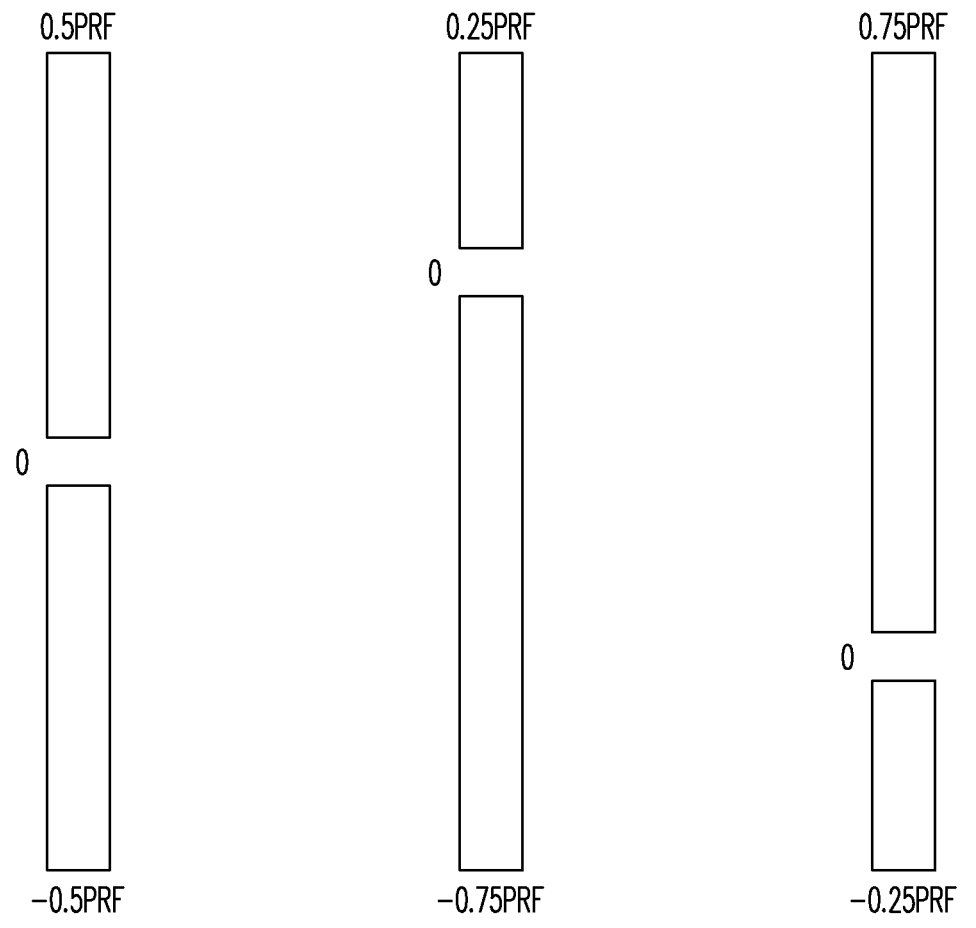

In a particular example as shown in FIG. 11C, a Doppler shift frequency range of $$-\frac{f_{PRF}}{4}$$

to $$\frac{3 f_{PRF}}{4}$$

reflects a baseline shift of $$-\frac{f_{PRF}}{4}.$$

This Doppler frequency range is associated with a negative maximum velocity corresponding to $$-\frac{f_{PRF}}{4}$$

and a positive maximum velocity corresponding to $$\frac{3f_{PRF}}{4}.$$

Similarly, a Doppler shift frequency range of $$-\frac{3f_{PRF}}{4}$$

to $$\frac{f_{PRF}}{4}$$

reflects a baseline shift of $$\frac{f_{PRF}}{4}$$

as shown in FIG. 11B. This Doppler frequency range is associated with a negative maximum velocity corresponding to $$-\frac{3f_{PRF}}{4}$$

and a positive maximum velocity corresponding to $$\frac{f_{PRF}}{4}.$$

Figure 1B:
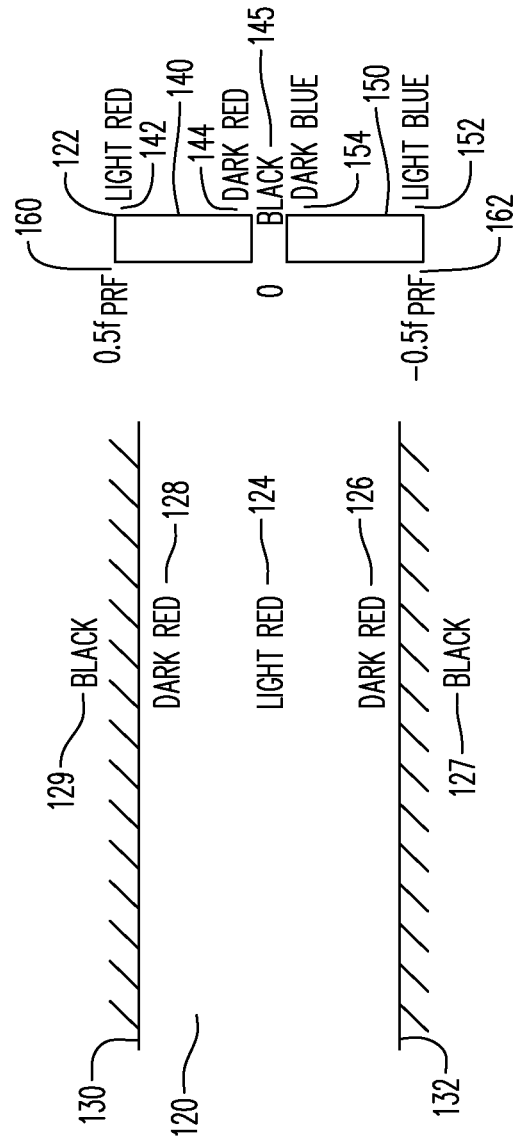
FIG. 1B: Non-aliased color Doppler image corresponding to the velocity distribution in FIG. 1A.
Figure 2A:
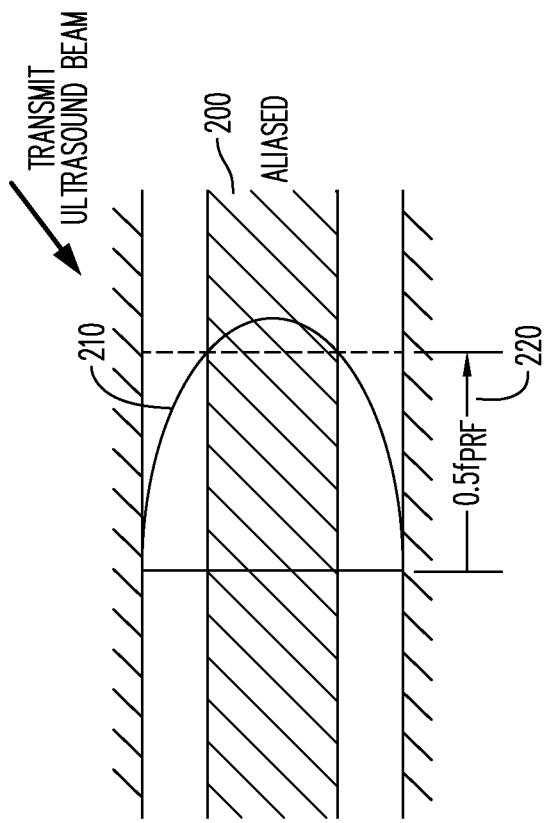
FIG. 2A: Blood velocity distribution in a vessel and transmit ultrasound beam direction.
Figure 2B:
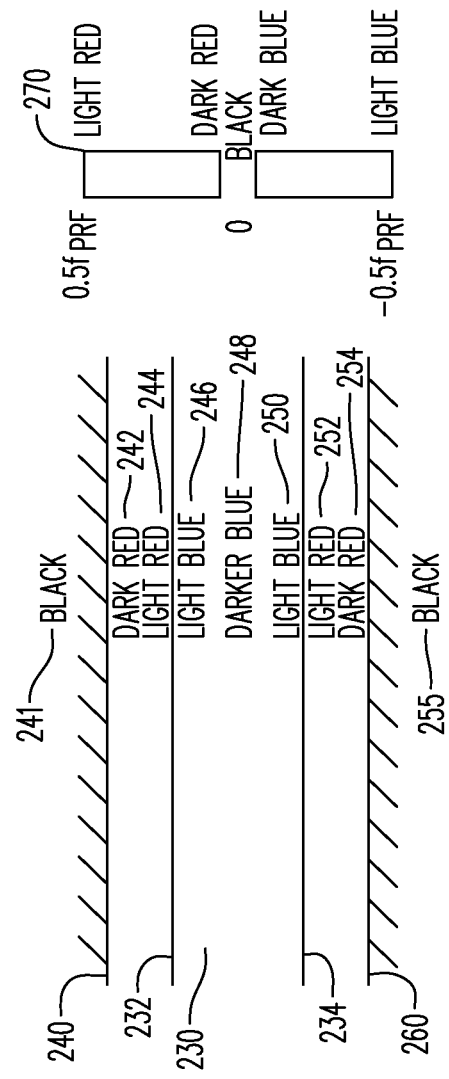
FIG. 2B: Aliased color Doppler image corresponding to the velocity distribution in FIG. 2A.

FIG. 11A corresponds to the Doppler shift frequency ranges of FIG. 1B and FIG. 2B, in which the baseline (i.e., 0 Hz) is in the center of the Doppler shift frequency (velocity) scale. When the baseline is shifted, e.g. by $$\frac{f_{PRF}}{4}$$

as shown in FIG. 11B, the positive maximum frequency becomes $$\frac{f_{PRF}}{4}$$

while the negative maximum frequency becomes $$-\frac{3f_{PRF}}{4}.$$

If the baseline shift is $$-\frac{f_{PRF}}{4},$$

the positive maximum frequency becomes $$\frac{3f_{PRF}}{4}$$

while the negative maximum frequency decreases to $$-\frac{f_{PRF}}{4}$$

as shown in FIG. 11C. In other words, the positive maximum frequency is decreased by the baseline shift while the absolute magnitude of the negative maximum frequency is increased by the baseline shift.

Often in cardiovascular applications, as well as in other applications, blood velocities may exceed these maximum velocities, resulting in aliasing. Color Doppler imaging uses color coding methods to display blood velocities (or corresponding Doppler shift frequencies) in colors. With respect to FIG. 1B, the positive velocities may be displayed in shades of red 140, with higher positive velocities represented by lighter red 142 and lower positive velocities represented by darker red 144, while the negative velocities may be displayed in shades of blue 150, with higher negative velocities represented by lighter blue 152 and lower negative velocities represented by darker blue 154. Other color coding methods can be used to represent blood flow velocities.

FIG. 1B depicts a Doppler shift frequency range of $$-\frac{f_{PRF}}{2}$$

to $$\frac{f_{PRF}}{2}.$$

Therefore, the Doppler data of FIG. 1B is associated with a baseline shift of 0 Hz (i.e., no baseline shift). As mentioned above, embodiments are not limited thereto.

When aliasing occurs, the color flow image may "wrap around" at velocities corresponding to the positive maximum frequency 160, with velocities corresponding to frequencies which exceed the positive maximum frequency 160 represented by colors associated with negative velocities (e.g., shades of blue). Conversely, aliasing may cause velocities corresponding to frequencies which exceed (in absolute value) the negative maximum frequency 162 to be represented by colors associated with positive velocities (e.g., shades of red). Aliasing therefore complicates the blood velocity image and makes any diagnosis based thereon difficult.

FIG. 1A shows a typical blood velocity distribution 102 within a vessel 100. At the vessel walls 104, 106, blood flow velocities are generally zero due to non-slip conditions and according to the laws of fluid mechanics. Blood velocities increase with position away from the walls. Generally, the velocity is the highest near the center of vessel 108. A good example is a parabolic velocity distribution which is defined as $$V = V_{MAX}\left\{1 - \left(\frac{r}{R_a}\right)^2\right\}, \quad (5)$$

where V is velocity 114 at radial position r 110, $R_a$ is radius 112 and $V_{MAX}$ is the maximum velocity 116 in the vessel center. The velocity distribution is smooth as the velocity changes gradually across the lumen radius 112. Assuming the maximum velocity 116 corresponds to a Doppler shift frequency that is less than the $$\frac{f_{PRF}}{2},$$

color Doppler technique may produce a color flow image 120 as represented in FIG. 1B, although colors cannot be reproduced in this black and white document using the color coding 122 methods described previously. The transmit ultrasound beam 118 is pointing towards the blood flow as shown in FIG. 1A. Color flow image area 124 at the vessel center is light red while color flow image areas 126, 128 close to the vessel walls 130, 132 are dark red. This color flow image 120 is not aliased, and therefore does not exhibit any "wrap around" transitions from light red to light blue or light blue to light red as described previously.

On the other hand, FIG. 2A shows a case in which some velocities of blood flow velocity distribution 210 correspond to a frequency greater than the positive or negative maximum frequencies (in this example, $$-\frac{f_{PRF}}{2}$$

or $$\frac{f_{PRF}}{2}).$$

These blood flow velocities may therefore be aliased as depicted in FIG. 2B. Specifically, the corresponding color flow image 230 of FIG. 2B exhibits transitions 232, 234 from light red to light blue. From the near wall side 240, the flow image 230 shows dark red 242, light red 244, light blue 246, darker blue 248, light blue 250, light red 252 and dark red 254 in colors. Color flow image 230 is therefore an inaccurate portrayal of velocity distribution 210 due to aliasing.

Figure 10:
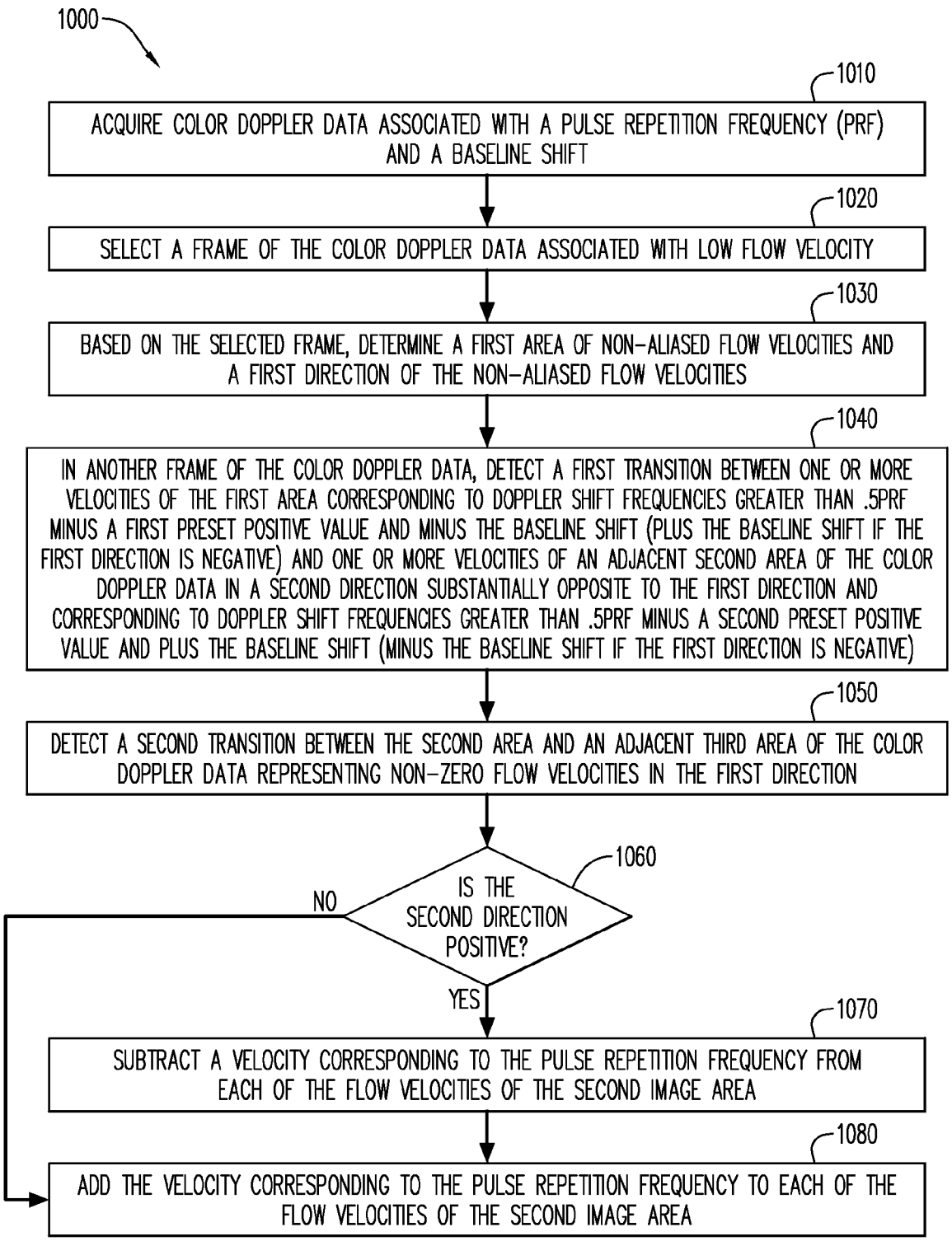
FIG. 10: A flow diagram of a process to address aliasing according to some embodiments.

FIG. 10 is a flow diagram of a process 1000 to address aliasing according to some embodiments. Process 1000 may be embodied in any combination of hardware and/or software. In one example, process 1000 is embodied in processor-executable process steps stored on a tangible medium. Process 1000 may be executed by a correction unit as will be described below with respect to FIGS. 4 and 5.

It should be understood that process 1000 describes the processing of one contiguous aliased image area. Accordingly, a system according to some embodiments may process non-aliased image areas differently. A system according to some embodiments may also or alternatively process multiple aliased image areas by executing process 1000 more than once.

Initially, at 1010, color Doppler data associated with a pulse repetition frequency is acquired. As used herein, "color Doppler data" may refer to color flow line data or color Doppler image data (e.g., scan-converted image data) generated from such color flow line data. Accordingly, process 1000 may be performed on either type of Doppler data.

The color Doppler data acquired at 1010 is also associated with a baseline shift. For simplicity, the foregoing example assumes a baseline shift of 0 Hz, which corresponds to a Doppler shift frequency range of $$-\frac{f_{PRF}}{2}$$

to $$\frac{f_{PRF}}{2}.$$

As described above, the acquired color Doppler data may be generated based on sampled data as shown in equation 2. The frequency of these samples is equal to the pulse repetition frequency mentioned at 1010.

Next, at 1020, a frame of the color Doppler data associated with a low flow velocity is detected. Blood flow is pulsatile and changes its velocity from zero to a maximum as the heart pumps blood, depending on the phase in the cardiac cycle. At the peak systole, blood velocity is the highest in major arteries such as the aorta. In the diastolic period, the aortic valve of the heart is closed and blood velocity is zero or close to zero.

Figure 12:
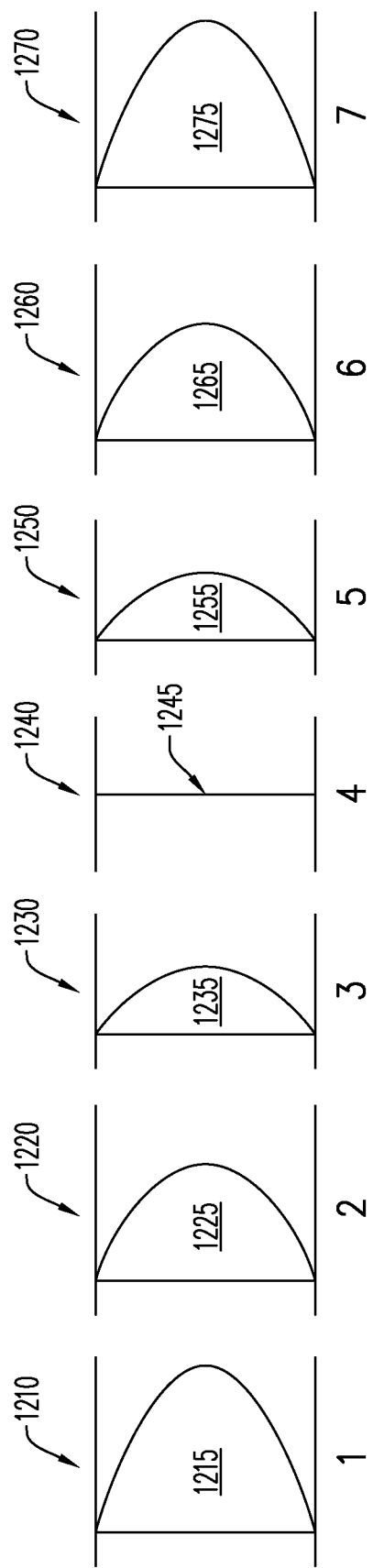
FIG. 12: Diagram of pulsatile velocities

FIG. 12 shows a typical time sequence (t=1-7) of blood flow velocities across a vessel. At time 4 (frame #4, 1240), blood flow velocities 1245 are virtually zero while blood flow velocities 1275 are the maximum at time 7 (frame #7, 1270). In some embodiments of 1020, a color flow image frame is selected from a plurality of color flow image frames associated with different times. The selected color flow image exhibits lower flow velocities than any other one of the plurality of color flow image frames.

Most ultrasound imaging systems are equipped with a cine memory to store images, often in a line data format, as the line data require less memory space than a scan-converted image. Therefore, a sequence of color flow image frames may be already stored in the cine memory prior to 1020, and these color flow image frames may be accessed and processed to select the frame exhibiting the lowest velocities. Alternately, only new frames acquired in real-time may be processed at 1020 to find a color flow image frame exhibiting the lowest velocities.

In some embodiments of 1020, a region of interest (or an area of color flow) is selected and a velocity parameter is calculated for each of several frames. The velocity parameter may comprise any suitable parameter, including but not limited to mean color flow velocity, an absolute value of mean color flow velocity, mean of absolute color flow velocities, and number of non-black (i.e. non-zero velocity) color flow data samples. The frame is then selected at 1020 based on the velocity parameter of each frame. For example, the selected frame may be a frame that is associated with the lowest mean color flow velocity. If no color flow data samples exist in the selected frame, a neighboring frame in time is selected instead.

At 1030, and based on the selected frame, a first area of the color Doppler data which represents non-aliased flow velocities is detected. Also determined at 1030 is the direction of the non-aliased flow velocities, which will be referred to below as the "first" direction. In this regard, the flow velocity direction in first area is assumed to be correct and non-aliased because low velocities exhibit the highest probability of being represented without aliasing in the color Doppler data. In contrast, frames including higher flow velocities (e.g., frame #7, 1270) exhibit a higher probability of aliasing.

A first transition is detected in another frame of the color Doppler data at 1040. The first transition is a transition between one or more flow velocities of all or part of the previously-determined first area of the first flow direction corresponding to Doppler shift frequencies having magnitudes greater than half the pulse repetition frequency $$\left(\frac{f_{PRF}}{2}\right)$$

minus a first preset positive value and minus any baseline shift and one or more flow velocities of a second area of the color Doppler data. The flow velocities of the second area are in a second direction substantially opposite to the first direction and correspond to Doppler shift frequencies having magnitudes greater than half the pulse repetition frequency $$\left(\frac{f_{PRF}}{2}\right)$$

minus a second preset positive value and plus the baseline shift. The first preset positive value may be equal to or different from the second preset positive value.

The above description of 1040 assumes that the flow velocities of the first area are in a direction toward the ultrasound transducer used to obtain the sampled data (i.e., the first direction is "positive"). If the flow velocities of the first area are in a direction away from ultrasound transducer (i.e., the first direction is negative), the first transition is detected between one or more flow velocities of the second area corresponding to Doppler shift frequencies having magnitudes greater than half the pulse repetition frequency $$\left(\frac{f_{PRF}}{2}\right)$$

minus a first preset positive value and plus any baseline shift and one or more flow velocities of the second area in a second direction substantially opposite to the first direction and corresponding to Doppler shift frequencies having magnitudes greater than half the pulse repetition frequency $$\left(\frac{f_{PRF}}{2}\right)$$

minus a second preset positive value and minus the baseline shift. Again, the first preset positive value may be equal to or different from the second preset positive value.

Analysis and correction of color flow image 230 of FIG. 2B will now be described with respect to process 1000. It will be assumed that the first area determined in the "reference" frame at 1030 is the area including flow velocities 242 and 244 of color flow image 230. It will also be assumed that the determined first direction is the same as shown in color flow image 230 (i.e., positive, or towards the transducer).

Accordingly, at 1040, transition 232 is detected as a transition between one or more flow velocities (244) corresponding to Doppler shift frequencies having magnitudes greater than half the pulse repetition frequency $$\left(\frac{f_{PRF}}{2}\right)$$

minus a first preset positive value (and minus a 0 Hz baseline shift since the first direction is positive in the present example) and one or more flow velocities (246) of a second area in a second direction substantially opposite to the first direction and corresponding to Doppler shift frequencies having magnitudes greater than half the pulse repetition frequency $$\left(\frac{f_{PRF}}{2}\right)$$

minus a second preset positive value (and plus the 0 Hz baseline shift since the second direction is negative in the present example). Unlike the velocities (244, 246) immediately adjacent to the first transition, the magnitude of some velocities (e.g., 242) of the first area and some velocities (e.g., 248) of the second area might not exceed the above-described thresholds.

A second transition is detected in the frame under analysis at 1050. The second transition lies between the second area and an adjacent third area of the color Doppler data. The third area represents non-zero flow velocities in the first direction. Transition 234 of image 230 is an example of such a second transition according to some embodiments.

By virtue of the foregoing, it is determined that the second area between the first and second transitions is aliased. To correct the aliasing, it is determined at 1060 whether the second direction is positive (i.e., toward the ultrasound transducer used to obtain the sampled data). If so, the second area is corrected at 1070 by subtracting a velocity value corresponding to a Doppler shift frequency of the pulse repetition frequency from each velocity of the second area. If the second direction is not positive, the second area is corrected at 1080 by adding the velocity value corresponding to a Doppler shift frequency of the pulse repetition frequency to each velocity of the second area.

Figure 6B:
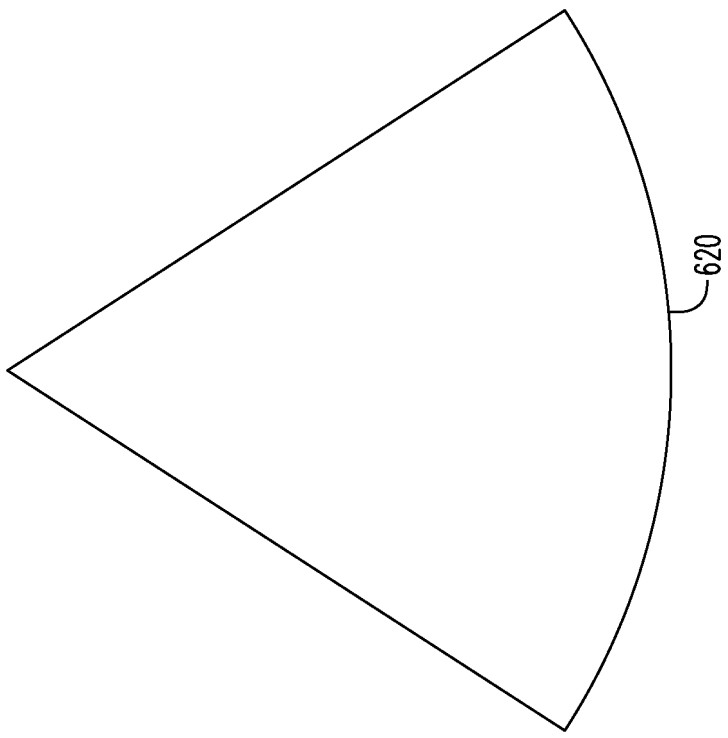
FIG. 6B: A representation of a scan-converted color flow image.
Figure 6A:
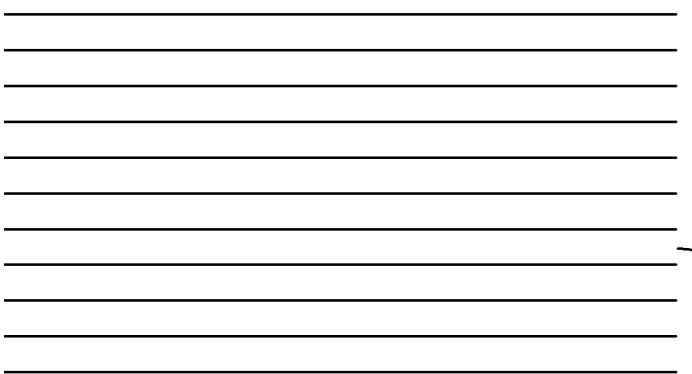
FIG. 6A: A representation of color flow lines.
Figure 7B:
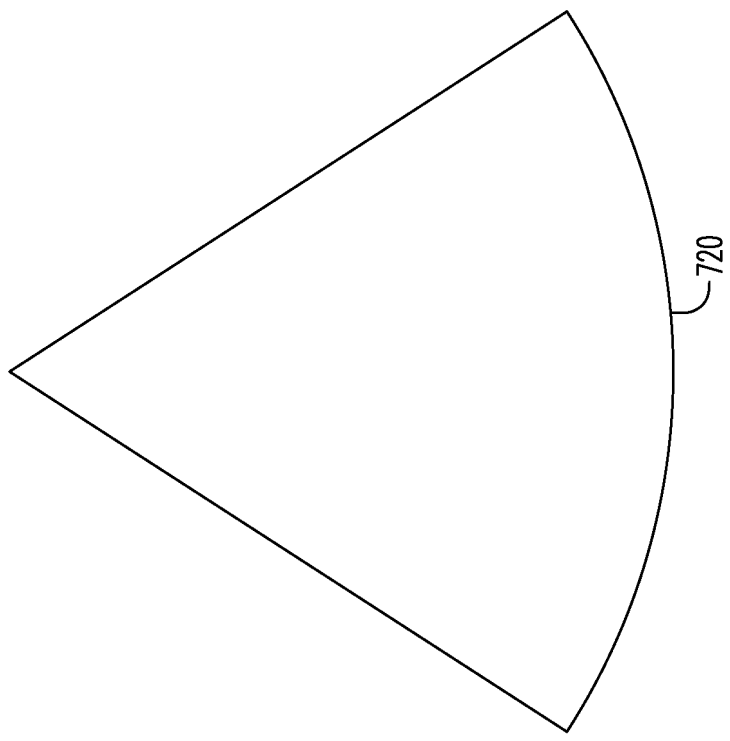
FIG. 7B: A representation of a scan-converted B-mode image.
Figure 7A:
FIG. 7A: A representation of B-mode lines.

As mentioned above, process 1000 may be applied to color flow line data or color Doppler image data according to some embodiments. FIG. 6A shows color flow lines 600 before scan-conversion, although only 11 lines are shown as an example. A color flow line consists of many color flow data samples along the line. Color flow lines are created from color beam data and may not show correct spatial dimensions. Scan-conversion is a technique to convert the color flow lines to a raster video image by interpolating the color flow lines. In a scan-converted image (e.g., sector scan) shown FIG. 6B, the color flow image consists of color flow image pixels of the orthogonal (x-y) coordinate with the correct length relationship (vertical vs. horizontal dimensions) in contrast to the color flow lines shown in FIG. 6A. B-mode imaging also uses the scan-conversion technique to convert B-mode lines as shown in FIG. 7A to a B-mode image as shown in FIG. 7B by interpolating B-mode line data.

Process 1000 may begin at a near or far field in some embodiments. Alternately, process 1000 may be performed from both near and far fields.

Embodiments of process 1000 may operate upon color flow lines 800 by one line at a time as shown in FIG. 8A, where color flow data samples are represented by dots 820. More specifically, process 1000 may proceed from one end of a color flow line to another end and then onto the next color flow line until the last color flow line is processed. A color flow line 800 represents many color flow data samples 820 in a color flow beam.

In some embodiments, process 1000 is performed horizontally across color flow lines 840 as shown in FIG. 8B, using color flow line data samples 830. Process 1000 may be performed diagonally across color flow lines 860 as shown in FIG. 8C, using the color flow line data samples 850.

Figure 9B:
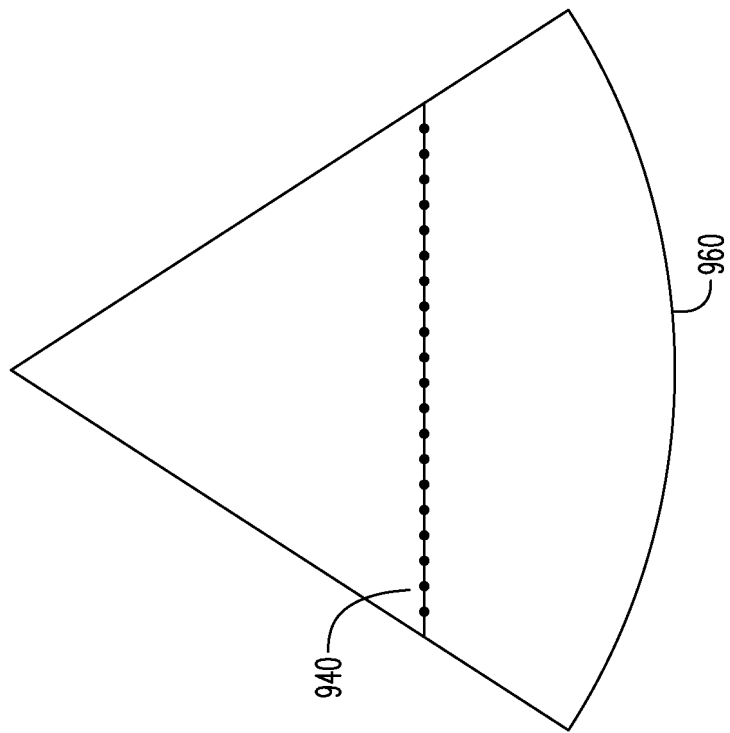
FIG. 9B: Aliasing detection in horizontal direction using a color flow image.
Figure 9A:
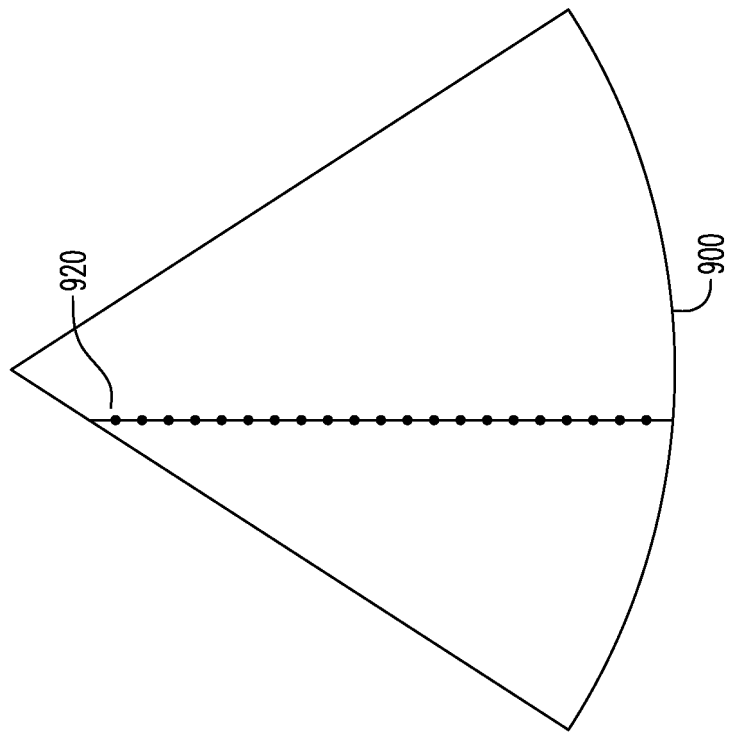
FIG. 9A: Aliasing detection in vertical direction using a color flow image.
Figure 9C:
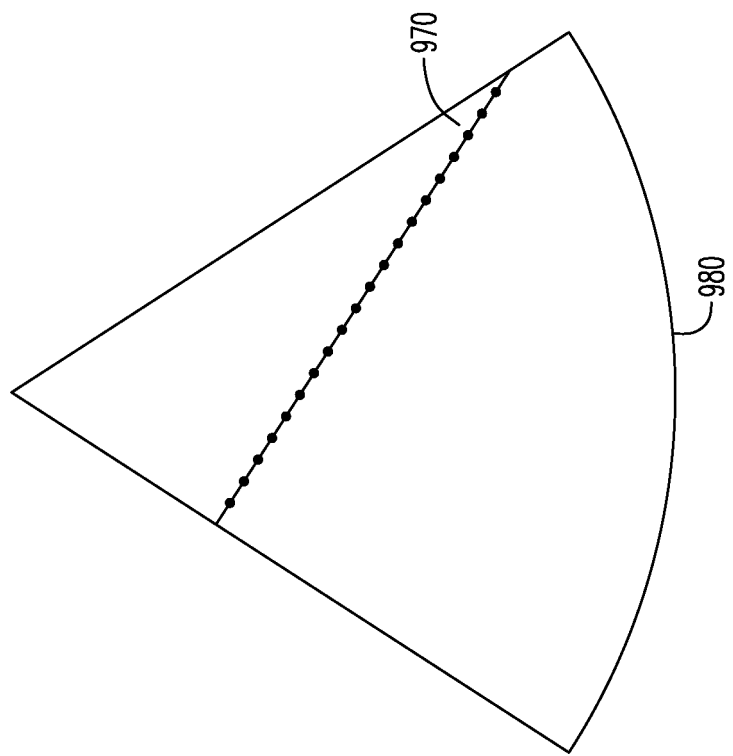
FIG. 9C: Aliasing detection in a diagonal direction using a color flow image.

Process 1000, in some embodiments, is performed on a scan-converted color flow image 620 pixel by pixel. The color flow image 620 is obtained by scan-converting the color flow lines 600. In some embodiments, as shown in FIG. 9A using color flow data samples 920, process 1000 is performed vertically from top to bottom in a first color flow image column and moves onto the next column until the last column is reached. Alternately, as shown in FIG. 9B using color flow data samples 940, process 1000 may be performed horizontally. As shown in FIG. 9C, using color flow data samples 970, process 1000 may be performed diagonally across a color flow image 980. The path traversed by a process according to some embodiments may be a straight line or a curve.

In an alternate embodiment, aliasing correction is performed over the temporal domain rather than the spatial domain. At a given spatial point in a frame under analysis, the aliasing test is performed over next-neighboring frames. Specifically, transitions between velocities are detected across frames at a same spatial point, rather than within a single frame across a two-dimensional space.

Figure 13:
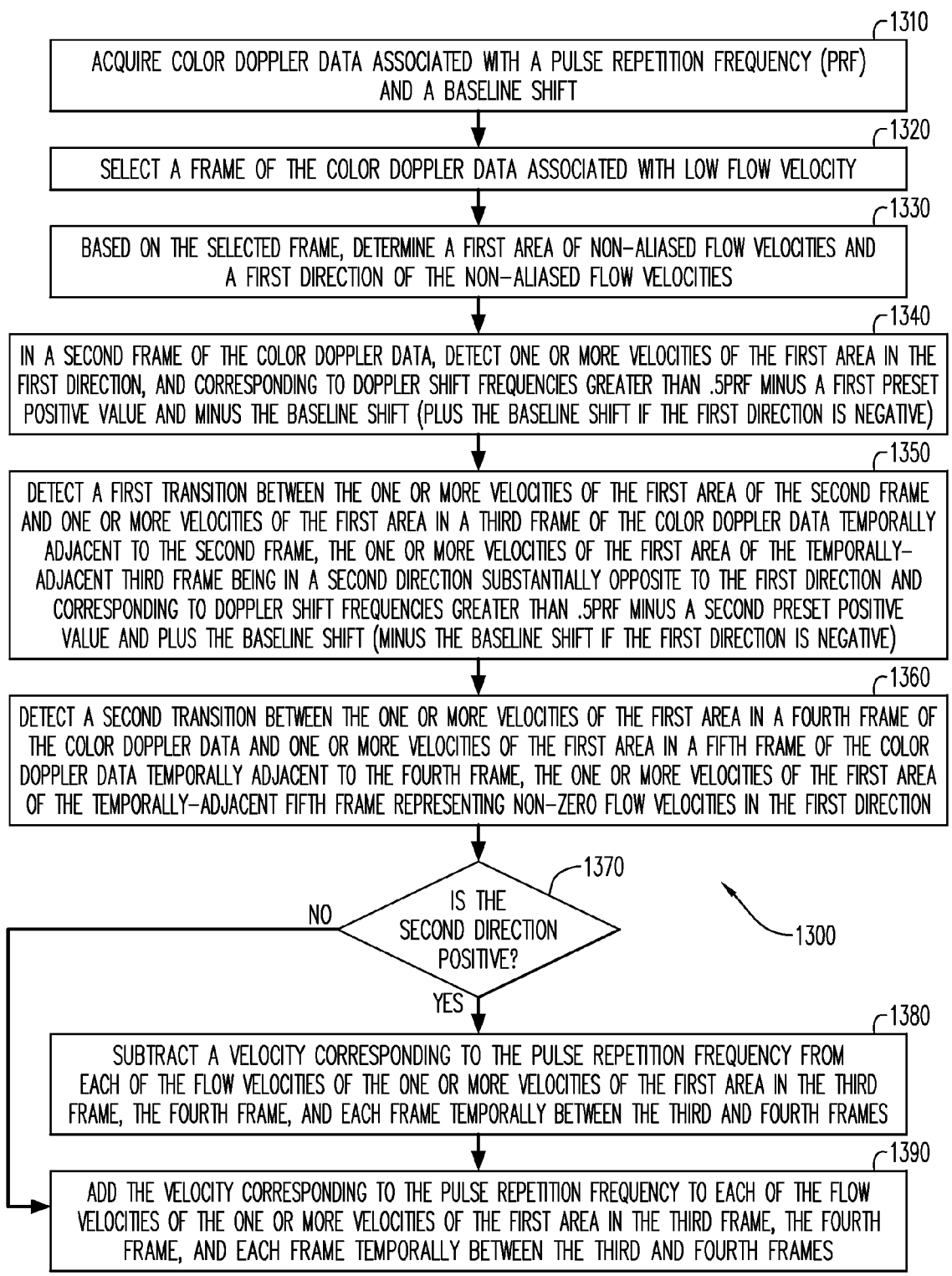
FIG. 13: A flow diagram of a process to address aliasing according to some embodiments.

Process 1300 of FIG. 13 illustrates an example of aliasing detection over the temporal domain. First, at 1310, color Doppler data associated with a pulse repetition frequency ($f_{PRF}$) and a baseline shift is acquired. At 1320, a frame of the color Doppler data associated with low flow velocity is selected. Most ultrasound imaging systems are equipped with a cine memory to store images, often in a line data format, as the line data require less memory space than a scan-converted image. Therefore, a sequence of color flow image frames may be already stored in the cine memory prior to 1320, and these color flow image frames may be accessed and processed to select the frame exhibiting the lowest velocities. Alternately, only new frames acquired in real-time may be processed at 1320 to find a color flow image frame exhibiting the lowest velocities.

In some embodiments of 1320, a region of interest (or an area of color flow) is selected and a velocity parameter is calculated for each of several frames. The velocity parameter may comprise any suitable parameter, including but not limited to mean color flow velocity, an absolute value of mean color flow velocity, mean of absolute color flow velocities, and number of non-black (i.e. non-zero velocity) color flow data samples. The frame is then selected at 1320 based on the velocity parameter of each frame. For example, the selected frame may be a frame that is associated with the lowest mean color flow velocity. If no color flow data samples exist in the selected frame, a neighboring frame in time is selected instead.

A first area of non-aliased flow velocities and a first direction of the non-aliased flow velocities are determined based on the selected frame at 1330. Accordingly, 1310, 1320 and 1330 may proceed as described above with respect to 1010, 1020 and 1030.

Next, at 1340, one or more velocities of the first area and in the first direction are detected in a second frame of the color Doppler data, the one or more velocities corresponding to Doppler shift frequencies greater than $$\frac{f_{PRF}}{2}$$

minus a first positive preset value minus the baseline shift if the first direction is positive or plus the baseline shift if the first direction is negative. A first transition is then detected at 1350 between the one or more velocities of the first area in the second frame and one or more velocities of the first area in a third frame of the color Doppler data temporally-adjacent to the second frame, where the one or more velocities of the first area in the temporally-adjacent third frame is in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive.

A second transition is detected at 1360. The second transition is between the one or more velocities of the first area in a fourth frame of the color Doppler data and one or more velocities of the first area in a fifth frame of the color Doppler data temporally-adjacent to the fourth frame, where the one or more velocities of the first area in the temporally-adjacent fifth frame represent non-zero flow velocities in the first direction. Aliasing is therefore determined to exist in the first area of each frame temporally between (and including) the third frame and the fourth frame.

To correct this aliasing, it is determined at 1370 whether the second direction is positive (i.e., toward the ultrasound transducer used to obtain the sampled data). If so, a velocity value corresponding to a Doppler shift frequency of the pulse repetition frequency is subtracted from each of the one or more velocities of the first area in the third frame, the fourth frame, and the frames temporally between the third frame and the fourth frame. If the second direction is not positive, a velocity value corresponding to a Doppler shift frequency of the pulse repetition frequency is added to each of the one or more velocities of the first area in the third frame, the fourth frame, and the frames temporally between the third frame and the fourth frame.

Such a temporal-based aliasing test and subsequent correction may be performed throughout the color flow area. Alternatively, since the first direction represents a true flow direction in the first area, any colors of frames which represent the opposite flow direction in the first area may be considered aliased and subjected to correction as described above.

Figure 3:
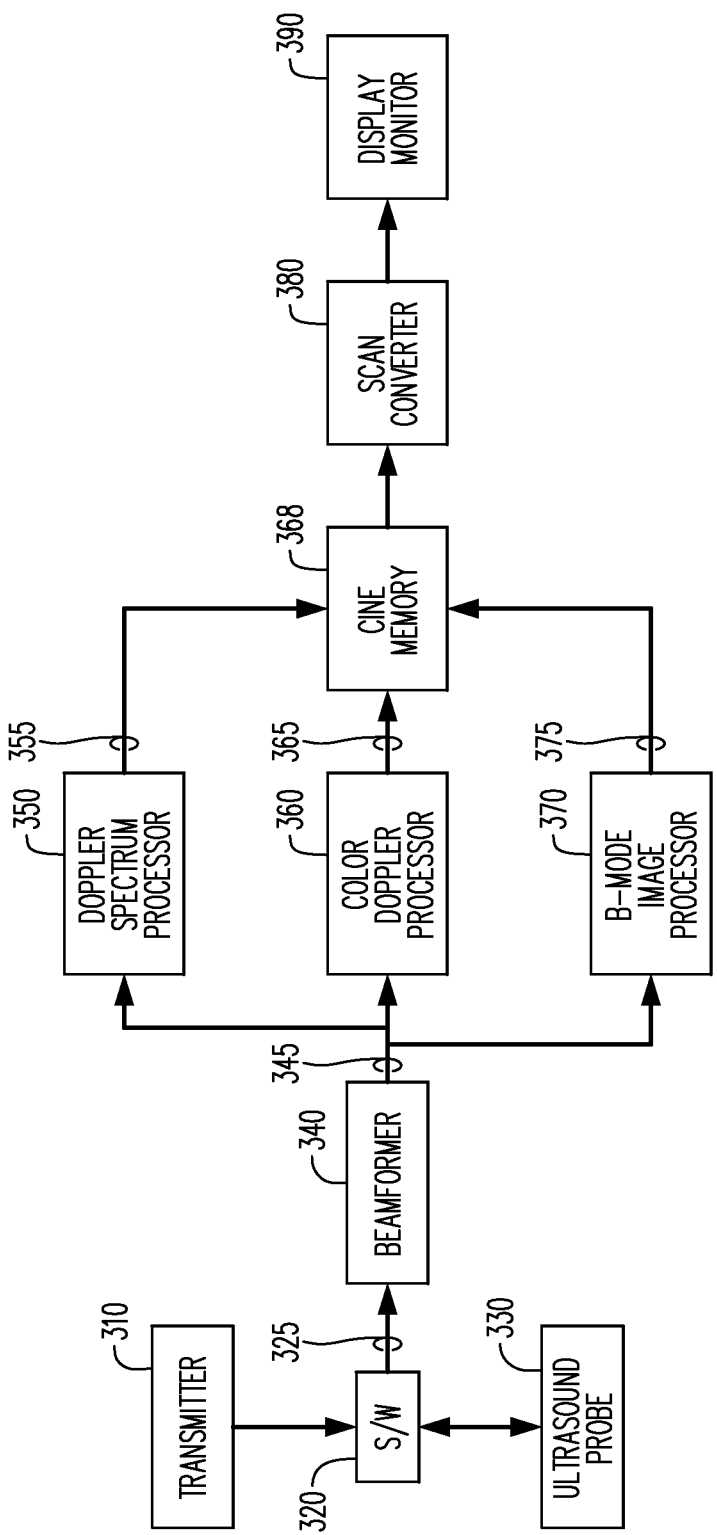
FIG. 3: A diagram of an ultrasound diagnostic imaging system (prior art).

FIG. 3 shows a diagram of a conventional ultrasound diagnostic imaging system with B-mode imaging, Doppler spectrum and color Doppler imaging (e.g., see U.S. Pat. No. 4,573,477, U.S. Pat. No. 4,622,977, U.S. Pat. No. 4,641,668, U.S. Pat. No. 4,651,742, U.S. Pat. No. 4,651,745, U.S. Pat. No. 4,759,375, U.S. Pat. No. 4,766,905, U.S. Pat. No. 4,768,515, U.S. Pat. No. 4,771,789, U.S. Pat. No. 4,780,837, U.S. Pat. No. 4,799,490, and U.S. Pat. No. 4,961,427). The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter 310 through a transmit/receive switch 320. The probe 320 may consist of an array of transducer elements which are separately driven by the transmitter with different time-delays so that a transmit ultrasound beam is focused and steered. A beamformer 340 receives the received ultrasound signal(s) from the probe 330 through the switch 320 and processes the signal(s) 325. The beamformer applies delays and/or phases to the signals and the resultant signals are summed for focusing and steering a receive ultrasound beam. The beamformer may also apply apodization, amplification and filtering.

The processed signal 345 is coupled to a Doppler spectrum processor 350, a color flow processor 360, and a B-mode image processor 370. The Doppler spectrum processor 350 includes a Doppler signal processor and a spectrum analyzer, and processes Doppler flow velocity signals and calculates and outputs a Doppler spectrum 355. The color flow processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color flow processor signals (velocity, power, and variance) 365 and B-mode processor signals 375 are coupled to a cine memory 368 which stores multiple frames of data and is coupled to a scan converter 380 that converts the signals to scan-converted signals. The first memory location in the cine memory 368 may be considered a real-time memory as it holds the newest data. As a real-time or newest frame data is stored in the cine memory 368, older frame data shifts through the memory locations of the cine memory 368. Therefore, the last memory location in the cine memory 368 holds the oldest frame data. The output of scan converter 380 is coupled to a display monitor 390 for displaying ultrasound images.

Figure 4:
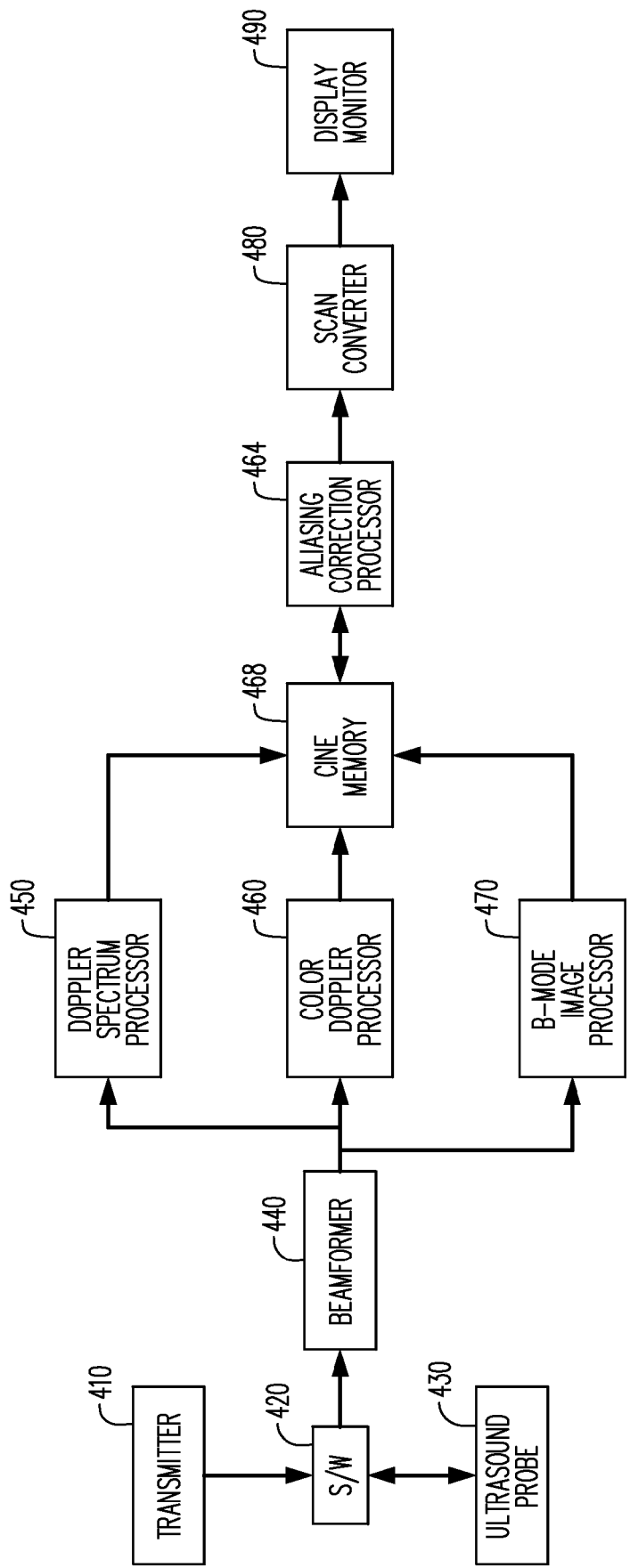
FIG. 4: A diagram of an ultrasound diagnostic imaging system according to some embodiments and using line data.
Figure 5:
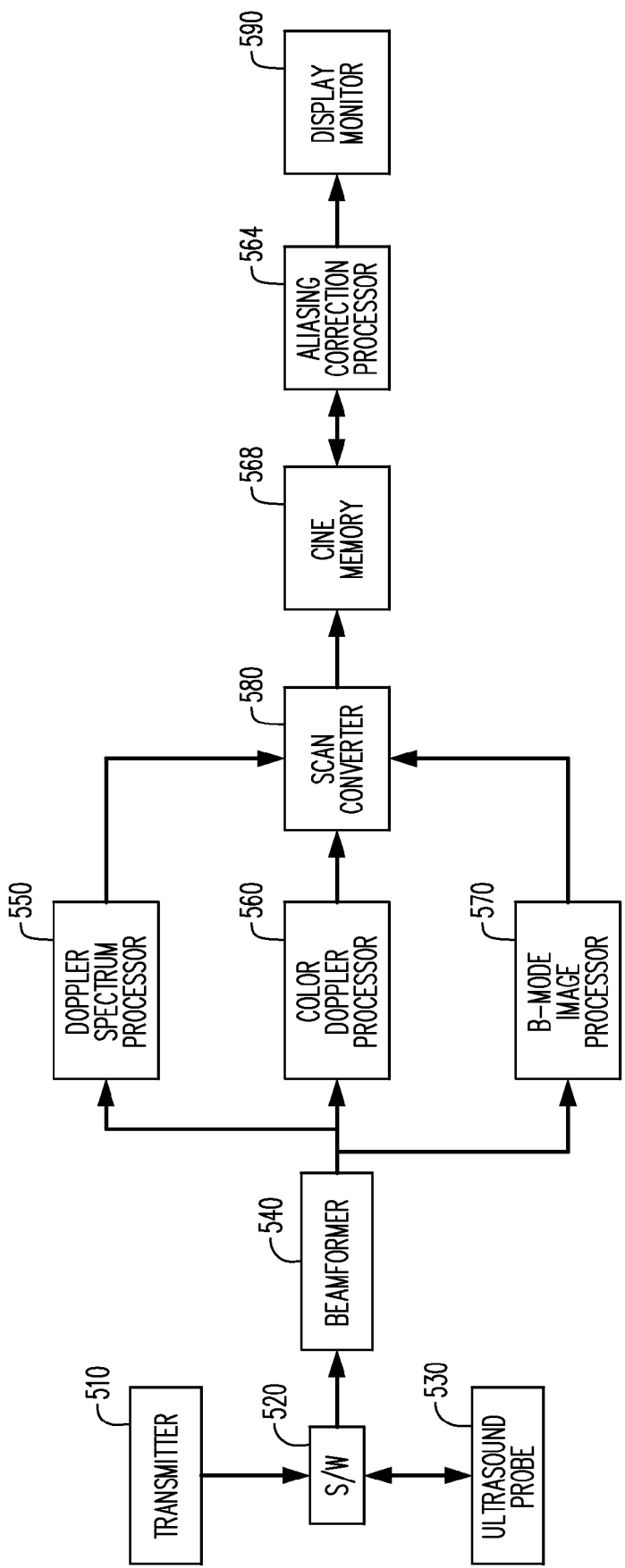
FIG. 5: A diagram of an ultrasound diagnostic imaging system according to some embodiments and using scan-converted images.

FIG. 4 shows a diagram of an ultrasound imaging system including a color Doppler aliasing correction processor 464 according to some embodiments. The aliasing correction processor 464 may perform process 1000 or 1300 with respect to color flow line data as described previously. The aliasing correction processor 464 may access color Doppler line data stored in a cine memory 468 or a real-time memory (e.g., the first memory in the cine memory 468) and then may perform the aliasing correction process 1000 or 1300 and may send the corrected color Doppler line data to a scan converter 480. The aliasing correction processor 464 may also write the corrected data into the cine memory 468 . . . FIG. 5 shows a diagram of embodiments in which the testing and correction of color Doppler aliasing is performed in the scan-converted image domain rather than the line data domain which was discussed previously. The B-mode image and color Doppler image are scan-converted and stored in a cine memory 568 before the aliasing correction processor 564 performs the process 1000 or 1300 thereon to correct aliasing. The corrected color Doppler data may be sent to the display monitor 590 and also may be written into the cine memory 568.

One or more embodiments have been described. Nevertheless, various modifications will be apparent to those in the art.

What is claimed is:

1. A non-transitory medium storing processor-executable process steps for correcting aliasing, the process steps executable to:

acquire color Doppler data with a pulse repetition frequency ($f_{PRF}$) and a baseline shift;

select a frame of the color Doppler data with a flow velocity substantially equal to a lowest flow velocity of the color Doppler data;

based on the selected frame, determine a first area of non-aliased flow velocities and a first direction of the non-aliased flow velocities;

detect, in another frame of the color Doppler data, a first transition between one or more velocities of the first area corresponding to Doppler shift frequencies greater than $$\frac{f_{PRF}}{2}$$

minus a first positive preset value minus the baseline shift if the first direction is positive or plus the baseline shift if the first direction is negative and one or more velocities of an adjacent second area of the color Doppler data in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive;

detect a second transition between the second area and an adjacent third area of the color Doppler data representing non-zero flow velocities in the first direction;

subtract a velocity corresponding to a Doppler shift frequency of $f_{PRF}$ from each of the flow velocities of the second area if the second direction is positive; and add the velocity corresponding to a Doppler shift frequency of $f_{PRF}$ to each of the flow velocities of the second area if the second direction is negative.

2. A medium according to claim 1, wherein selection of the frame of the color Doppler data associated with low flow velocity comprises:

for each of a plurality of frames of the color Doppler data, calculation of a velocity parameter associated with a common area; and determination of one of the plurality of frames that is associated with a smallest one of the calculated velocity parameters.

3. A medium according to claim 2, wherein the velocity parameter comprises one of a mean velocity, an absolute value of mean color flow velocity, a mean of the absolute color flow velocities, a number of non-zero velocity data samples in the common area.

4. A medium according to claim 1, wherein the color Doppler data comprises color flow line data.

5. A medium according to claim 1, wherein the color Doppler data comprises scan-converted color flow image data.

6. A medium according to claim 1, wherein the selected frame and the another frame are stored in cine-memory.

7. A medium according to claim 1, wherein the baseline shift is greater than or equal to $$-\frac{f_{PRF}}{2}$$

and less than or equal to $$\frac{f_{PRF}}{2}.$$

8. A system comprising:
an aliasing correction processor to:
acquire color Doppler data with a pulse repetition frequency ($f_{PRF}$) and a baseline shift;
select a frame of the color Doppler data with a flow velocity substantially equal to a lowest flow velocity of the color Doppler data;
based on the selected frame, determine a first area of non-aliased flow velocities and a first direction of the non-aliased flow velocities;
detect, in another frame of the color Doppler data, a first transition between one or more velocities of the first area corresponding to Doppler shift frequencies greater than $$\frac{f_{PRF}}{2}$$

minus a first positive preset value minus the baseline shift if the first direction is positive or plus the baseline shift if the first direction is negative and one or more velocities of an adjacent second area of the color Doppler data in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive;
detect a second transition between the second area and an adjacent third area of the color Doppler data representing non-zero flow velocities in the first direction;
subtract a velocity corresponding to a Doppler shift frequency of $f_{PRF}$ from each of the flow velocities of the second area if the second direction is positive; and
add the velocity corresponding to a Doppler shift frequency of $f_{PRF}$ to each of the flow velocities of the second area if the second direction is negative.

9. A system according to claim 8, wherein selection of the frame of the color Doppler data associated with low flow velocity comprises:
for each of a plurality of frames of the color Doppler data, calculation of a velocity parameter associated with a common area; and
determination one of the plurality of frames that is associated with a smallest one of the calculated velocity parameters.

10. A system according to claim 9, wherein the velocity parameter comprises one of a mean velocity, an absolute value of mean color flow velocity, a mean of the absolute color flow velocities, a number of non-zero velocity data samples in the common area.

11. A system according to claim 8, further comprising a color Doppler processor to provide the color Doppler data to the aliasing correction processor,
wherein the color Doppler data comprises color flow line data.

12. A system according to claim 8, further comprising a scan converter to provide the color Doppler data to the aliasing correction processor,
wherein the color Doppler data comprises scan-converted color flow image data.

13. A system according to claim 8, wherein the baseline shift is greater than or equal to $$-\frac{f_{PRF}}{2}$$

and less than or equal to $$\frac{f_{PRF}}{2}.$$

14. A non-transitory medium storing processor-executable process steps for correcting aliasing, the process steps executable to:
acquire color Doppler data with a pulse repetition frequency ($f_{PRF}$) and a baseline shift;
select a frame of the color Doppler data with a flow velocity substantially equal to a lowest flow velocity of the color Doppler data;
based on the selected frame, determine a first area of non-aliased flow velocities and a first direction of the non-aliased flow velocities;
detect one or more velocities of the first area and in the first direction in a second frame of the color Doppler data, the one or more velocities corresponding to Doppler shift frequencies greater than $$\frac{f_{PRF}}{2}$$

minus a first positive preset value minus the baseline shift if the first direction is positive or plus the baseline shift if the first direction is negative;
detect a first transition between the one or more velocities of the first area in the second frame and one or more velocities of the first area in a third frame of the color Doppler data temporally-adjacent to the second frame, the one or more velocities of the first area in the temporally-adjacent third frame being in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive;

detect a second transition between the one or more velocities of the first area in a fourth frame of the color Doppler data and one or more velocities of the first area in a fifth frame of the color Doppler data temporally-adjacent to the fourth frame, the one or more velocities of the first area in the temporally-adjacent fifth frame representing non-zero flow velocities in the first direction;

subtract a velocity corresponding to a Doppler shift frequency of $f_{PRF}$ from each of the flow velocities of the one or more velocities of the first area in the third frame, the fourth frame, and each frame temporally between the third and fourth frames if the second direction is positive; and add the velocity corresponding to a Doppler shift frequency of $f_{PRF}$ to each of the flow velocities of the one or more velocities of the first area in the third frame, the fourth frame, and each frame temporally between the third and fourth frames if the second direction is negative.

15. A medium according to claim 14, wherein selection of the frame of the color Doppler data associated with low flow velocity comprises:

for each of a plurality of frames of the color Doppler data, calculation of a velocity parameter associated with a common area; and determination of one of the plurality of frames that is associated with a smallest one of the calculated velocity parameters.

16. A medium according to claim 15, wherein the velocity parameter comprises one of a mean velocity, an absolute value of mean color flow velocity, a mean of the absolute color flow velocities, a number of non-zero velocity data samples in the common area.

17. A medium according to claim 14, wherein the color Doppler data comprises color flow line data.

18. A medium according to claim 14, wherein the color Doppler data comprises scan-converted color flow image data.

19. A medium according to claim 14, wherein the selected frame, the second frame, the third frame, the fourth frame and the fifth frame are stored in cine-memory.

20. A system comprising:

an aliasing correction processor to:

acquire color Doppler data with a pulse repetition frequency ($f_{PRF}$) and a baseline shift;

select a frame of the color Doppler data with a flow velocity substantially equal to a lowest flow velocity of the color Doppler data;

based on the selected frame, determine a first area of non-aliased flow velocities and a first direction of the non-aliased flow velocities;

detect one or more velocities of the first area and in the first direction in a second frame of the color Doppler data, the one or more velocities corresponding to Doppler shift frequencies greater than $$\frac{f_{PRF}}{2}$$

minus a first positive preset value minus the baseline shift if the first direction is positive or plus the baseline shift if the first direction is negative;

detect a first transition between the one or more velocities of the first area in the second frame and one or more velocities of the first area in a third frame of the color Doppler data temporally-adjacent to the second frame, the one or more velocities of the first area in the temporally-adjacent third frame being in a second direction substantially opposite to the first direction and corresponding to Doppler shift frequencies greater than $$\frac{f_{PRF}}{2}$$

minus a second positive preset value plus the baseline shift if the second direction is negative or minus the baseline shift if the second direction is positive;

detect a second transition between the one or more velocities of the first area in a fourth frame of the color Doppler data and one or more velocities of the first area in a fifth frame of the color Doppler data temporally-adjacent to the fourth frame, the one or more velocities of the first area in the temporally-adjacent fifth frame representing non-zero flow velocities in the first direction;

subtract a velocity corresponding to a Doppler shift frequency of $f_{PRF}$ from each of the flow velocities of the one or more velocities of the first area in the third frame, the fourth frame, and each frame temporally between the third and fourth frames if the second direction is positive; and add the velocity corresponding to a Doppler shift frequency of $f_{PRF}$ to each of the flow velocities of the one or more velocities of the first area in the third frame, the fourth frame, and each frame temporally between the third and fourth frames if the second direction is negative.

21. A system according to claim 20, wherein selection of the frame of the color Doppler data associated with low flow velocity comprises:

for each of a plurality of frames of the color Doppler data, calculation of a velocity parameter associated with a common area; and determination one of the plurality of frames that is associated with a smallest one of the calculated velocity parameters.

22. A system according to claim 21, wherein the velocity parameter comprises one of a mean velocity, an absolute value of mean color flow velocity, a mean of the absolute color flow velocities, a number of non-zero velocity data samples in the common area.

23. A system according to claim 20, wherein the color Doppler data comprises color flow line data.

24. A system according to claim 20, wherein the color Doppler data comprises scan-converted color flow image data.

25. A system according to claim 20, wherein the selected frame, the second frame, the third frame, the fourth frame and the fifth frame are stored in cine-memory.

* * * * *